United States Patent [19]

Chiulli

[11] 4,051,844
[45] Oct. 4, 1977

[54] TELESCOPING NEUROSURGICAL SCALP RETRACTOR

[75] Inventor: Robert D. Chiulli, Somerville, Mass.

[73] Assignee: Medico Developments, Inc., Boxford, Mass.

[21] Appl. No.: 684,295

[22] Filed: May 7, 1976

[51] Int. Cl.² ............................................. A61B 17/02
[52] U.S. Cl. ............................................................ 128/20
[58] Field of Search .................... 128/20, 303 R, 346, 128/76 B, 76 R; 32/40

[56] References Cited

U.S. PATENT DOCUMENTS

| 590,460 | 9/1897 | Mehlig | 128/20 |
|---|---|---|---|
| 1,799,554 | 4/1931 | Graves | 128/20 |
| 2,575,204 | 11/1951 | Brown | 128/76 B |
| 2,701,562 | 2/1955 | Michael et al. | 128/20 |
| 3,857,386 | 12/1974 | Ashbell | 128/20 |

FOREIGN PATENT DOCUMENTS 387,300   9/1922   Germany ............................. 128/20

Primary Examiner—Robert W. Michell
Assistant Examiner—Henry S. Layton
Attorney, Agent, or Firm—Scott R. Foster

[57] ABSTRACT

A neurosurgical scalp retractor for use in surgical operations within the skull, the retractor comprising an elongated frame, a first connector member at one end of the frame for attachment to the scalp, an extensible member connected to the frame, a releasable lock for fixing the extensible member in a desired position, and a second connector member disposed at a free end of the extensible member for attachment to an operating table drape.

2 Claims, 2 Drawing Figures

U.S. Patent    Oct. 4, 1977    4,051,844
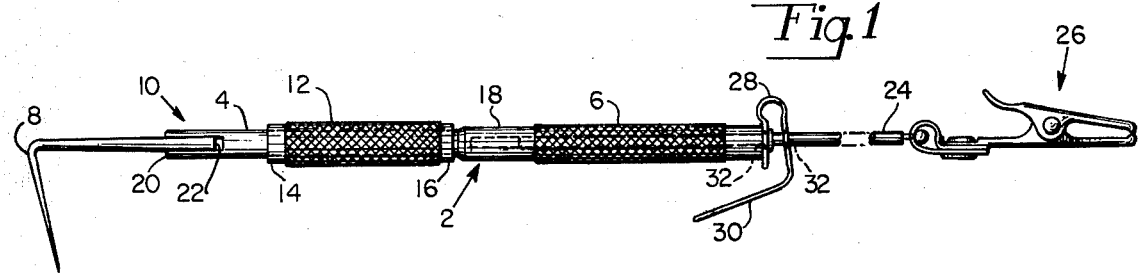
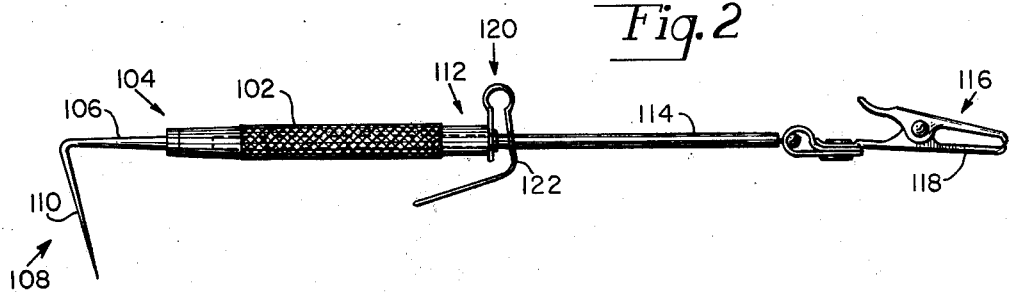

TELESCOPING NEUROSURGICAL SCALP RETRACTOR

BACKGROUND OF THE INVENTION

1. Field of the Invention

This invention relates to surgical devices and is directed more particularly to a neurosurgical scalp retractor for retaining an excised scalp in a position removed from the skull so that the skull is free and clear for an operation thereon and therein. 2. Description of the Prior Art In surgical operations within the human skull, it is customary that the person being operated upon be placed face-up on a table with his entire body covered with drapes except for the uppermost portion of the head. An incision is made about the sides and transversely across the scalp, such that the scalp may be reflected from the skull remaining attached to the body at the forward portion of the head. The scalp is reflected forwardly of the head and upwardly of the table, remaining attached by a living hinge to the head in the general region of the forehead. The free uppermost portion of the scalp is then secured to a drape so as to hold the scalp in an out-of-the-way position.

The device used to retain the scalp in the retracted position has generally been of a makeshift character. It is not uncommon to find sutures, rubber bands, and drape clamps used in varying combinations as means to retain the scalp.

SUMMARY OF THE INVENTION

An object of the present invention is to provide a neurosurgical scalp retractor which is economical to manufacture, easily sterilized, and simple and reliable in operation.

With the above and other objects in view, as will hereinafter appear, a feature of the present invention is the provision of a scalp retractor comprising an elongated frame, a first conductor means at one end of the frame for attachment to a scalp, an extensible member connected to the frame, releasable lock means on the device for holding the extensible member in a desired position, and second connector means disposed at a free end of the extensible member for attachment to a sheet.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWING

Reference is made to the accompanying drawing in which is shown an illustrative embodiment of the invention from which its novel features and advantages will be apparent.

FIG. 1 is an elevational view of one form of scalp retractor illustrative of an embodiment of the invention; and FIG. 2 is an elevational view of an alternative form of scalp retractor.

DESCRIPTION OF THE PREFERRED EMBODIMENT

Referring to FIG. 1, it will be seen that the illustrative device includes a frame 2 having a smaller cylindrically-shaped portion 4 and a larger cylindrically-shaped portion 6. At the free end of the smaller portion 4 there is disposed a first connector means, which may be a hook member 8 attached to the frame by a pivotal mounting means 10.

Slidably disposed on the smaller portion 4 of the frame 2 is a sleeve 12 having knurls thereon to facilitate handling. The sleeve 12 is provided with inside bevelled ends 14, 16. The sleeve 12 can be moved so that the bevelled end 16 engages a shoulder 18 interconnecting the smaller and larger portions of the frame. The sleeve 12 can also be moved so that the bevelled end 14 engages a shoulder 20 on a base portion 22 of the hook member 8. In the former position, the sleeve is removed from the pivotal mounting means 10 and the hook member 8 is free to pivot. In the latter position, the sleeve 12 covers the pivotal mounting means 10 and holds the hook member 8 rigidly in a fixed position.

Slidably disposed within the larger portion 6 of the frame 2 is a rod 24 having at its free end a second connector means which may be a clamp assembly 26 pivotally connected thereto. Fixed to the free end of the larger portion 6 of the frame 2 is a lock means which may be a U-shaped leaf spring 28 having a handle portion 30. The spring 28 has holes 32 therein through which passes the rod 24, the spring being bowed so as to exert a force against the rod 24, holding the rod in place. By application of pressure against the handle portion 30 of the spring 28, the force on the rod is released, permitting the rod to be slid in or out of the frame to selectively establish the length of the device.

The device is usually packaged or housed with the rod 24 disposed to the extent possible within the frame 2. The sleeve 12 abuts the shoulder 18 and the hook member 8 is pivoted at a 90° angle to the frame, thereby requiring a relatively small housing. In preparation for use, the device is removed from its housing (not shown) and, after approximate alignment of the hook axis with the axis of the frame, the sleeve 12 is moved so that the bevelled end 14 of the sleeve engages the shoulder 20 of the hook member base portion 22 to hold the sleeve in place by friction fit. The hook member 8 is thereby moved into a position as shown in FIG. 1 and locked in that position. The handle portion 30 of the spring 28 is pressed, releasing the rod 24 for sliding movement. The rod is brought to its maximum extension and the spring is released, locking the rod in this position. The device is then handed to the surgeon.

The surgeon enters the hook member 8 transversely through the subcutaneous tissues of the reflected scalp and positions the clamp 26 on a selected portion of a drape. He may shorten the extended length of the rod 24 by manipulation of the spring 28. The clamp 26 is engaged with a drape and the scalp thereby held. At any time during surgery that the drapes, scalp or combination thereof shift, the scalp retractor may be readjusted to maintain tension on the reflected scalp.

The device may be made of metal, if a permanent instrument is desired, or of a rigid plastic, or combination thereof, if a disposable instrument is desired. In the latter case, the hook member 8, spring 28, and clamp 26 are preferably of metal.

Referring to FIG. 2, it will be seen that the device may alternatively comprise a frame member 102 having at a first end 104 a shank 106 having at its free end a first attachment means 108, such as a hook means 110. A second end 112 of the frame 102 telescopically receives a rod 114 having at its free end second attachment means 116 which may be a clamp means 118. A locking means 120 is located on the frame member 102 and serves to exert a releasable locking force upon the rod 114 to secure the rod in a selected position of extension from the frame member 102. As discussed above, the locking means 120 may be in the form of a leaf spring 122. Thus, the alternative embodiment of FIG. 2 differs from the FIG. 1 embodiment in that the hook means is fixed in position relative to the frame member 2. The alternative embodiment is simpler and less costly to manufacture than the preferred embodiment and is particularly applicable to the field of disposable instruments.

It is to be understood that the present invention is by no means limited to the particular constructions herein disclosed and/or shown in the drawing, but also comprises any modifications or equivalents within the scope of the disclosure.

Having thus described my invention what I claim as new and desire to secure by Letters Patent of the United States is:

1. A neurosurgical scalp retractor comprising an elongated frame, a first connector means at one end of said frame, said first connector means having a sharp point for penetrating said scalp, a rigid extensible member comprising a rod slidably disposed in said frame, releasable lock means for fixing said extensible member in a selected position to selectively determine the extent of said retractor, said lock means comprising leaf spring means attached to said frame and adapted to releasably exert a force upon said extensible member to prevent movement of said extensible member relative to said frame, and second connector means disposed at a free end of said extensible member.

2. A neurosurgical scalp retractor comprising an elongated frame, a first connector member disposed at one end of said frame, said first connector member having a sharp point for penetrating said scalp and being pivotally connected to said frame, a sleeve slidably disposed on said frame and movable to a position to lock said first connector member in a desired attitude, a rigid extensible member connected to said frame, releasable lock means for fixing said extensible member in a selected position to selectively determine the extent of said retractor, and second connector means disposed at a free end of said extensible member.

* * * * *